US009572595B1

(12) United States Patent
Mantell

(10) Patent No.: US 9,572,595 B1
(45) Date of Patent: Feb. 21, 2017

(54) IN-DWELLING PORT FOR ACCESS INTO A BODY

(71) Applicant: Northgate Technologies Inc., Elgin, IL (US)

(72) Inventor: Robert R. Mantell, Arlington Heights, IL (US)

(73) Assignee: Northgate Technologies Inc., Elgin, IL (US)

( * ) Notice: Subject to any disclaimer, the term of this patent is extended or adjusted under 35 U.S.C. 154(b) by 0 days.

(21) Appl. No.: 14/638,605

(22) Filed: Mar. 4, 2015

Related U.S. Application Data

(60) Provisional application No. 61/948,342, filed on Mar. 5, 2014.

(51) Int. Cl.
| | |
|---|---|
| *A61M 39/04* | (2006.01) |
| *A61M 39/20* | (2006.01) |
| *A61B 17/34* | (2006.01) |
| *A61B 17/02* | (2006.01) |
| *A61B 17/04* | (2006.01) |
| *A61B 17/00* | (2006.01) |

(52) U.S. Cl.
CPC ....... *A61B 17/3431* (2013.01); *A61B 17/0218* (2013.01); *A61B 17/0401* (2013.01); *A61B 17/3415* (2013.01); *A61B 17/3423* (2013.01); *A61B 17/3498* (2013.01); *A61M 39/20* (2013.01); *A61B 2017/00889* (2013.01); *A61B 2017/00951* (2013.01); *A61B 2017/0225* (2013.01)

(58) Field of Classification Search
CPC ............ A61B 17/3498; A61B 17/3462; A61B 17/3421; A61B 17/3423; A61B 17/3431; A61B 17/3415; A61B 2017/00889; A61B 2017/3443; A61B 2017/3447; A61B 2017/3466; A61B 2017/3492; A61B 2017/3445; A61M 39/0247
USPC .......... 600/208, 201, 114; 604/204, 27, 174, 604/891.1, 513, 539, 164.01–164.06, 604/164.08; 607/40, 4; 606/213–216
See application file for complete search history.

(56) References Cited

U.S. PATENT DOCUMENTS

| | | | |
|---|---|---|---|
| 2,722,935 | A | 11/1955 | Thompson et al. |
| 3,464,434 | A | 9/1969 | Nielsen |
| 3,853,105 | A | 12/1974 | Kenagy |
| 3,862,907 | A | 1/1975 | Shimotsuma et al. |

(Continued)

FOREIGN PATENT DOCUMENTS

| | | |
|---|---|---|
| EP | 0 369 764 B1 | 6/1994 |
| EP | 0 692 273 B1 | 1/1996 |

(Continued)

OTHER PUBLICATIONS

International Search Report and Written Opinion of the International Searching Authority issued in international application No. PCT/IB2007/002249 on Sep. 10, 2008 (7 pages).

(Continued)

*Primary Examiner* — Pedro Philogene
(74) *Attorney, Agent, or Firm* — Brinks Gilson & Lione

(57) ABSTRACT

An in-dwelling port for providing repeated entry to a body during and/or after an operation is described. The port may include an external portion secured to a body outside an incision and a collapsible insertion portion that is inserted through the incision. The collapsible portion collapses when no instrument or lumen is present to permit the body to return to substantially a normal profile around the incision.

20 Claims, 16 Drawing Sheets

(56) References Cited

U.S. PATENT DOCUMENTS

| | | |
|---|---|---|
| 3,982,533 A | 9/1976 | Wiest |
| 4,048,992 A | 9/1977 | Lindemann et al. |
| 4,109,656 A | 8/1978 | Goethel et al. |
| 4,207,887 A | 6/1980 | Hiltebrandt et al. |
| 4,245,979 A | 1/1981 | Ito |
| 4,464,169 A | 8/1984 | Semm |
| 4,640,260 A | 2/1987 | Perez |
| 4,676,774 A | 6/1987 | Semm et al. |
| 4,691,900 A | 9/1987 | Maeda |
| 4,699,173 A | 10/1987 | Röhling |
| 4,878,894 A | 11/1989 | Sutter, Jr. et al. |
| 4,884,565 A | 12/1989 | Cocozza |
| 4,905,497 A | 3/1990 | Shindo et al. |
| 4,960,134 A | 10/1990 | Webster, Jr. |
| 4,977,776 A | 12/1990 | Shindo et al. |
| 4,984,564 A | 1/1991 | Yuen |
| 5,006,109 A | 4/1991 | Douglas et al. |
| 5,031,613 A | 7/1991 | Smith et al. |
| 5,061,239 A | 10/1991 | Shiels |
| 5,098,393 A | 3/1992 | Amplatz et al. |
| 5,121,700 A | 6/1992 | Blackwell et al. |
| 5,152,745 A | 10/1992 | Steiner et al. |
| 5,246,419 A | 9/1993 | Absten |
| 5,250,287 A | 10/1993 | Cocozza |
| 5,273,531 A | 12/1993 | Knoepfler |
| 5,292,304 A | 3/1994 | Mantell et al. |
| 5,305,698 A | 4/1994 | Blackwell et al. |
| 5,328,458 A | 7/1994 | Sekino et al. |
| 5,342,299 A | 8/1994 | Snoke et al. |
| 5,360,396 A | 11/1994 | Chan |
| 5,362,310 A | 11/1994 | Semm |
| 5,363,839 A | 11/1994 | Lankford |
| 5,383,923 A | 1/1995 | Webster, Jr. |
| 5,407,427 A | 4/1995 | Zhu et al. |
| 5,411,474 A | 5/1995 | Ott et al. |
| 5,411,988 A | 5/1995 | Bockow et al. |
| 5,439,441 A | 8/1995 | Grirnsley et al. |
| 5,464,008 A | 11/1995 | Kim |
| 5,478,837 A | 12/1995 | Rodgers et al. |
| 5,496,408 A | 3/1996 | Motoda et al. |
| 5,514,087 A | 5/1996 | Jones |
| 5,514,133 A * | 5/1996 | Golub ................ A61B 17/3423 604/175 |
| 5,534,261 A | 7/1996 | Rodgers et al. |
| 5,537,993 A | 7/1996 | Reichert et al. |
| 5,542,412 A | 8/1996 | Century |
| 5,554,112 A | 9/1996 | Walbrink et al. |
| 5,558,668 A | 9/1996 | Lankford et al. |
| 5,578,305 A | 11/1996 | Franz et al. |
| 5,586,974 A | 12/1996 | Martinez et al. |
| 5,599,297 A | 2/1997 | Chin et al. |
| 5,634,911 A | 6/1997 | Hermann et al. |
| 5,642,730 A | 7/1997 | Baran |
| 5,657,963 A | 8/1997 | Hinchliffe et al. |
| 5,664,560 A | 9/1997 | Merrick et al. |
| 5,728,223 A | 3/1998 | Murakami et al. |
| 5,800,381 A | 9/1998 | Ognier |
| 5,873,819 A | 2/1999 | Koch |
| 5,899,208 A | 5/1999 | Bonadio |
| 5,911,757 A * | 6/1999 | Seare, Jr. .............. A61F 2/0013 604/174 |
| 5,934,274 A | 8/1999 | Merrick et al. |
| 5,964,223 A | 10/1999 | Baran |
| 5,979,474 A | 11/1999 | Manako |
| 5,980,835 A | 11/1999 | Porozni |
| 6,024,736 A | 2/2000 | de la Torre et al. |
| 6,033,390 A * | 3/2000 | von Dyck ................ A61F 5/441 600/29 |
| 6,033,426 A | 3/2000 | Kaji |
| 6,051,241 A | 4/2000 | Briend et al. |
| 6,068,703 A | 5/2000 | Chen et al. |
| 6,076,745 A | 6/2000 | Primdahl |
| 6,079,413 A | 6/2000 | Baran |
| 6,085,556 A | 7/2000 | Moon |
| 6,092,364 A | 7/2000 | Stellwaqen |
| 6,116,240 A | 9/2000 | Merrick et al. |
| 6,165,201 A | 12/2000 | Sawhney et al. |
| 6,203,519 B1 | 3/2001 | Fagerstrom et al. |
| 6,240,943 B1 | 6/2001 | Smith |
| 6,267,746 B1 | 7/2001 | Blumbalough |
| 6,299,592 B1 | 10/2001 | Zander |
| 6,379,373 B1 | 4/2002 | Sawhney et al. |
| 6,428,500 B1 | 8/2002 | Koninckx |
| 6,526,976 B1 | 3/2003 | Baran |
| 6,537,246 B1 | 3/2003 | Unger et al. |
| 6,551,270 B1 | 4/2003 | Bimbo et al. |
| 6,579,279 B1 | 6/2003 | Rabiner et al. |
| 6,679,873 B2 | 1/2004 | Rabiner et al. |
| 6,719,960 B1 | 4/2004 | Hills et al. |
| 6,729,334 B1 | 5/2004 | Baran |
| 6,764,461 B2 | 7/2004 | Mickley et al. |
| 6,802,835 B2 | 10/2004 | Rabiner et al. |
| 6,821,287 B1 | 11/2004 | Jang |
| 6,872,189 B2 | 3/2005 | DeLegge |
| 6,896,665 B2 | 5/2005 | Picha et al. |
| 6,949,092 B1 | 9/2005 | Moss |
| 7,027,851 B2 | 4/2006 | Mejia |
| 7,052,454 B2 | 5/2006 | Taylor |
| 7,097,632 B2 | 8/2006 | Shia et al. |
| 7,163,510 B2 | 1/2007 | Kahle et al. |
| 7,172,085 B2 | 2/2007 | Beaudette |
| 7,195,590 B2 | 3/2007 | Butler et al. |
| 7,220,253 B2 | 5/2007 | Kantsevoy et al. |
| 7,255,675 B2 | 8/2007 | Gertner et al. |
| 7,300,399 B2 | 11/2007 | Bonadio et al. |
| 7,344,547 B2 | 3/2008 | Piskun |
| 7,367,963 B2 | 5/2008 | Cise et al. |
| 7,377,898 B2 | 5/2008 | Ewers et al. |
| 7,393,322 B2 | 7/2008 | Wenchell |
| 7,404,807 B2 | 7/2008 | Callaway |
| 7,452,347 B2 | 11/2008 | DeLegge |
| 7,470,251 B2 | 12/2008 | Shah |
| RE41,159 E | 3/2010 | Bourguignon |
| 7,670,279 B2 | 3/2010 | Gertner |
| 7,699,817 B2 | 4/2010 | Adams |
| 7,699,818 B2 | 4/2010 | Gilbert |
| 7,740,620 B2 | 6/2010 | Gilbert et al. |
| 7,744,308 B2 | 6/2010 | Bussey, Jr. et al. |
| 7,751,868 B2 | 7/2010 | Glossop |
| 7,771,396 B2 | 8/2010 | Stefanchik et al. |
| 7,794,436 B2 | 9/2010 | Pinel |
| 8,663,271 B2 | 3/2014 | Mantell |
| 2002/0068923 A1 | 6/2002 | Caldwell et al. |
| 2002/0082584 A1 | 6/2002 | Rosenman et al. |
| 2002/0183715 A1 | 12/2002 | Mantell et al. |
| 2004/0153027 A1 | 8/2004 | Mantell |
| 2005/0010164 A1 | 1/2005 | Mantell |
| 2005/0113858 A1* | 5/2005 | Deutsch ........... A61B 17/00491 606/195 |
| 2005/0125002 A1 | 6/2005 | Baran |
| 2005/0137529 A1 | 6/2005 | Mantell |
| 2005/0137592 A1 | 6/2005 | Nguyen et al. |
| 2007/0270654 A1 | 11/2007 | Pignato et al. |
| 2008/0086167 A1* | 4/2008 | Mastri ................ A61B 17/3421 606/198 |
| 2008/0103366 A1 | 5/2008 | Banchieri et al. |
| 2008/0147114 A1 | 6/2008 | Derowe et al. |
| 2011/0144448 A1* | 6/2011 | Shelton, IV ........ A61B 17/3423 600/216 |
| 2014/0200410 A1 | 7/2014 | Mantell |

FOREIGN PATENT DOCUMENTS

| | | |
|---|---|---|
| EP | 0 937 478 A1 | 8/1999 |
| EP | 0 712 635 B1 | 5/2003 |
| EP | 1 477 119 A1 | 11/2004 |
| FR | 2 840 222 | 12/2003 |
| JP | 5-168714 | 2/1993 |
| JP | 63-84243 | 6/1998 |
| WO | 93/17744 | 9/1993 |
| WO | 94/00484 | 1/1994 |
| WO | 96/29987 | 10/1996 |
| WO | 96/40090 | 12/1996 |
| WO | 00/69511 | 11/2000 |

(56) References Cited

FOREIGN PATENT DOCUMENTS

OTHER PUBLICATIONS

International Preliminary Report on Patentability issued in international application No. PCT/IB2007/002249 on Apr. 2, 2009 (5 pages).
Office Action issued in Canadian application No. 2,660,050, dated Apr. 15, 2013 (3 pages).

* cited by examiner

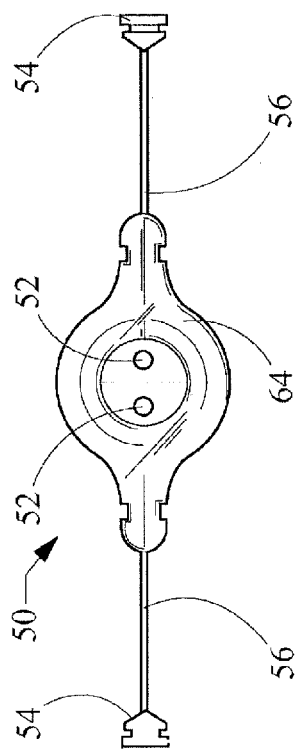
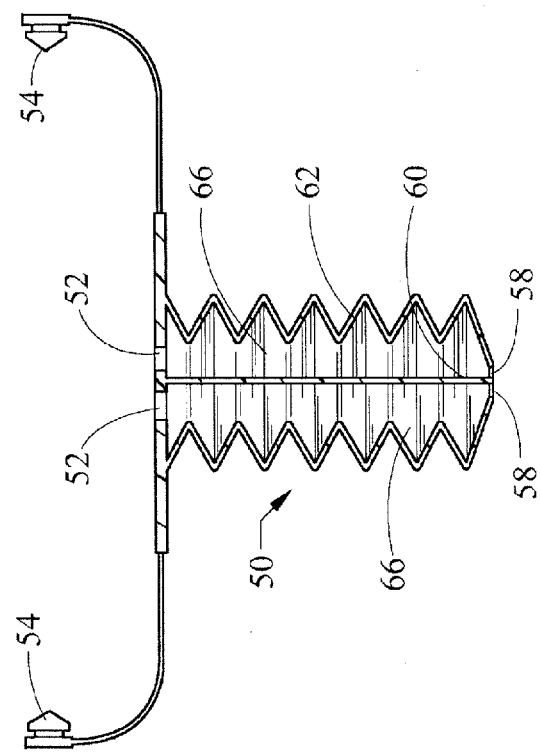
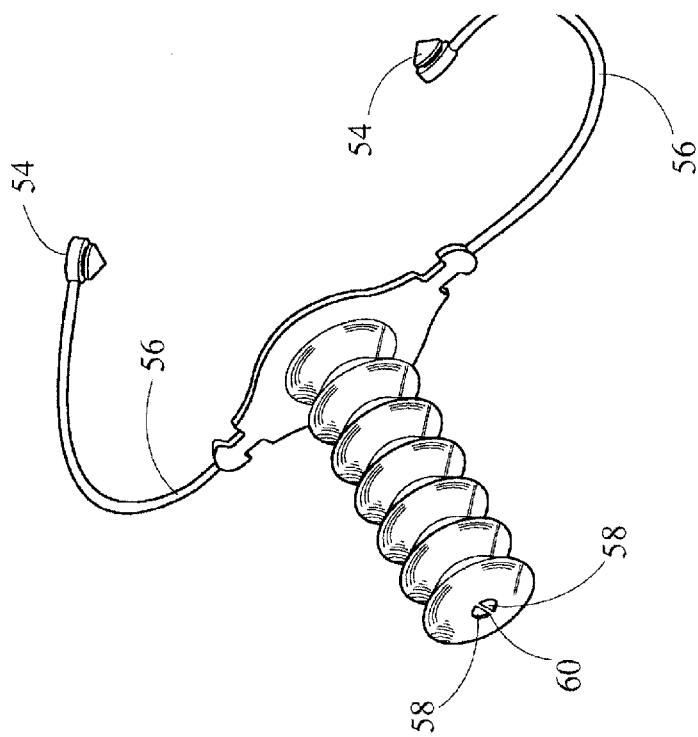
Fig. 10
Fig. 11
Fig. 12

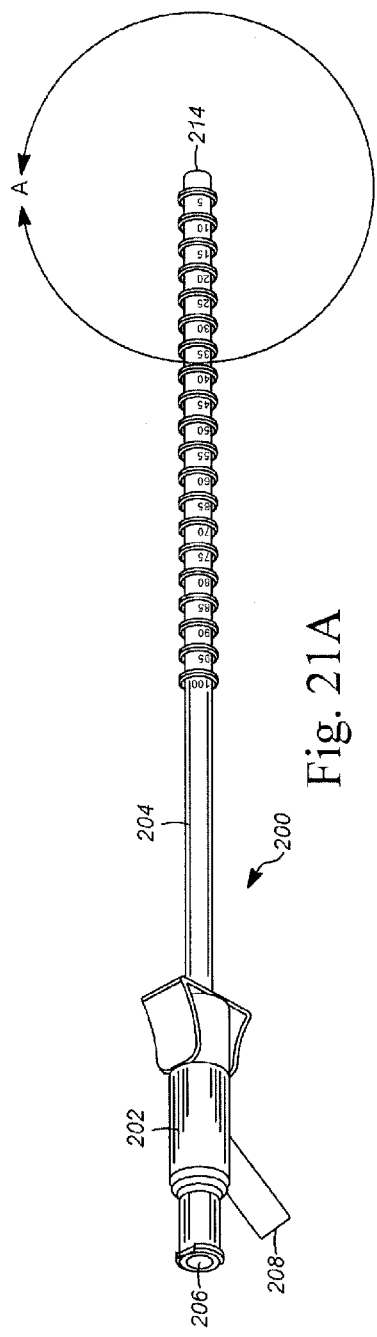
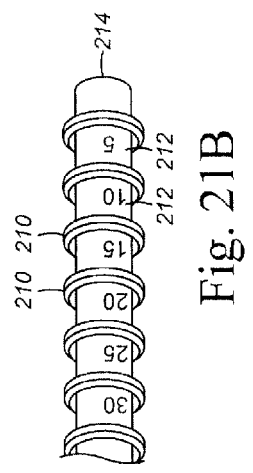
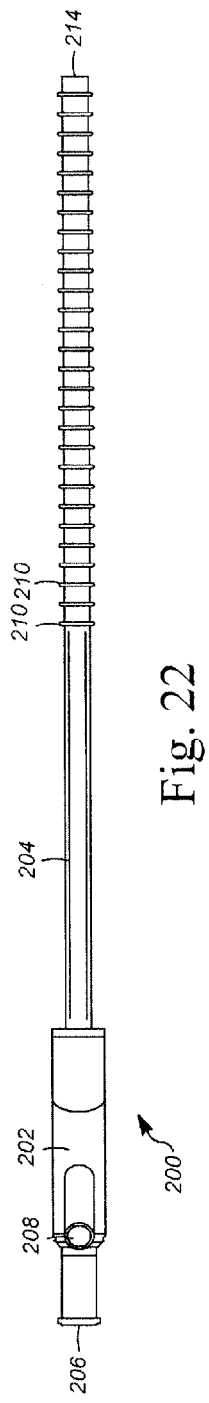
Fig. 21A
Fig. 21B
Fig. 22

IN-DWELLING PORT FOR ACCESS INTO A BODY

CROSS-REFERENCE TO RELATED APPLICATIONS

This application claims the benefit of U.S. Provisional Application No. 61/948,342, filed Mar. 5, 2014, the entirety of which is hereby incorporated herein by reference.

TECHNICAL FIELD

This application relates to medical devices for use in surgical applications. More specifically, this application relates to ports for use in accessing an area of a body during and/or after a surgical procedure.

BACKGROUND

In minimally invasive surgical procedures, such as laparoscopic procedures, one or more small incisions are made in a body to allow access for the necessary surgical tools. If there is a need to re-enter the body after a surgical procedure, a mechanism for doing so must be put in place. For targeted or prophylactic chemotherapy, post-operative applications of a substance can be made by re-instituting an environment in the patient in which subsequent applications of the substance may be made. This may be accomplished by leaving a port device in the patient after the surgical procedure, or by surgically placing a port in the patient in preparation of a non-surgical treatment regimen.

The port may be a device capable of providing a sanitary access point to a body, where the device is a resealable mechanism that attaches to the exterior of the skin and the interior wall of the skin. The port permits a device for applying a substance to the body to be reconnected to the patient at a later time to apply the substance or other treatment. One example of this type of port is an enteral feeding tube port.

The design of re-entry ports typically focuses on semi-rigid tubes, such as feeding ports which are meant to transverse from outside the body into an organ such as the stomach. These devices often have a bulb or protrusion at the insertion end to maintain the location of the tube in the organ being accessed, and consist of a rigid or semi-rigid tube or lumen. Catheters, such as urethral catheters for access into the bladder tend to be flexible catheters, usually with a balloon or some type of protrusion that is used to anchor the catheter into the organ to prevent its movement back through the body channel. Intravenous ports, ports or needles that are inserted into a vein, are generally taped or perhaps sutured in place to prevent the accidental removal of the device. Other devices such as flat tubes with holes, sometimes under suction have been used as drains for wounds or to prevent fluid buildup in the chest cavity.

SUMMARY

An improved port is described below that can remain in place, for example between physical structures such as the abdominal wall and the organs below, or in the plural cavity between the ribs and the lungs, or in any other physical location where the separation of bodily spaces may be required on a recurring basis.

According to a one aspect, an in-dwelling port is described having an external portion or flange configured for placement outside of an incision and defining a proximal port opening. An insertion portion includes a non-collapsible portion attached to the external portion and positioned in a substantially coaxial relationship to the proximal port opening, as well as a collapsible portion attached to the non-collapsible portion on one end and having a distal port opening on the other end. The collapsible insertion portion is repeatably adjustable between an elongated position, where the collapsible insertion portion defines an elongated length, and a collapsed or retracted position where the collapsible portion defines a collapsed length. The elongated length is greater than the collapsed length. In different embodiments, a membrane with a predefined slit may cover the proximal port opening. A pair of tethers fastened to the collapsible portion, passing through external portion or flange, and attaching on the outside of the flange opposite the insertion portion to a retaining ring may assist in retracting the collapsible portion evenly and repeatably. An inserter with a hollow tube sized to fit in the proximal port opening and wider than the distal port opening may be used to both extend and retract the collapsible portion in conjunction with the retaining ring and tethers.

Other features and advantages of the invention will become apparent upon review of the following drawings, detailed description and claims.

BRIEF DESCRIPTION OF THE DRAWINGS

FIG. 10 is a top plan view of a third alternative embodiment of the in-dwelling port of FIG. 1.

FIG. 11 is a cross-sectional side view of the port of FIG. 10 in an elongated position.

FIG. 12 is a perspective view of the port of FIG. 11.

FIGS. 21A-21B are views of an inserter usable with the in-dwelling port of FIGS. 19-20.

FIG. 22 is a side view of the inserter of FIG. 21A.

DETAILED DESCRIPTION

Figure 1:
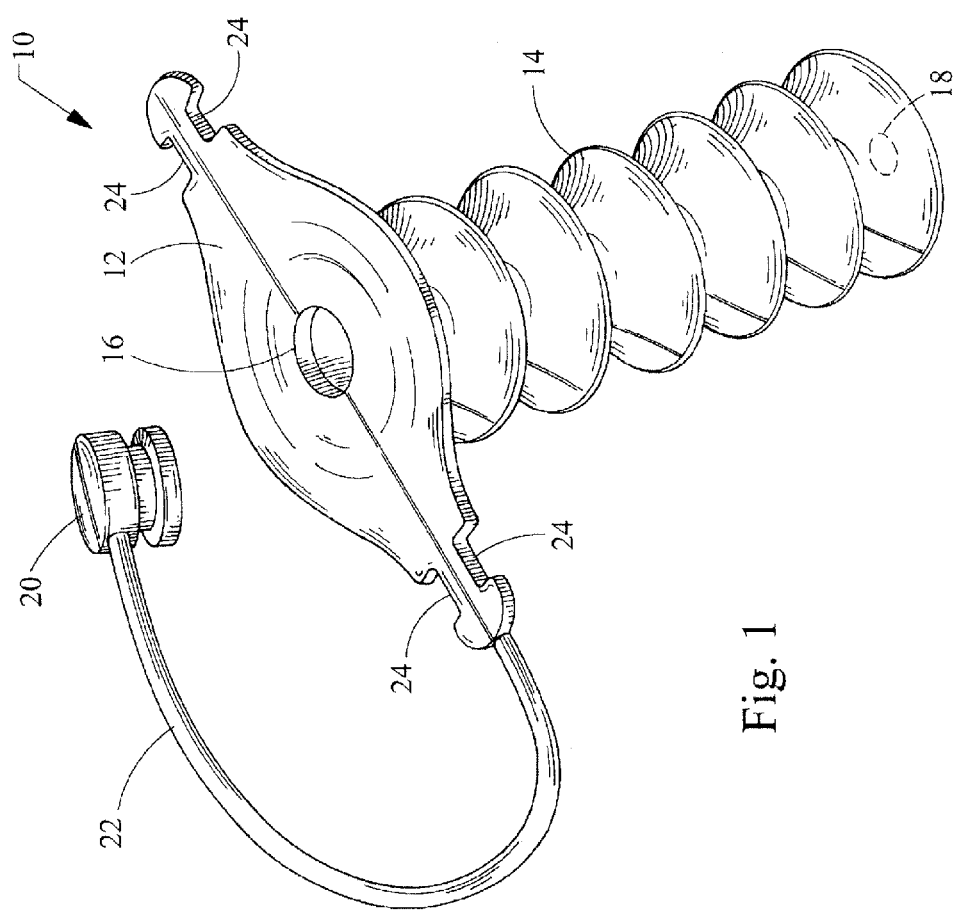
FIG. 1 is a perspective view of an in-dwelling port in an elongated position.
Figure 2:
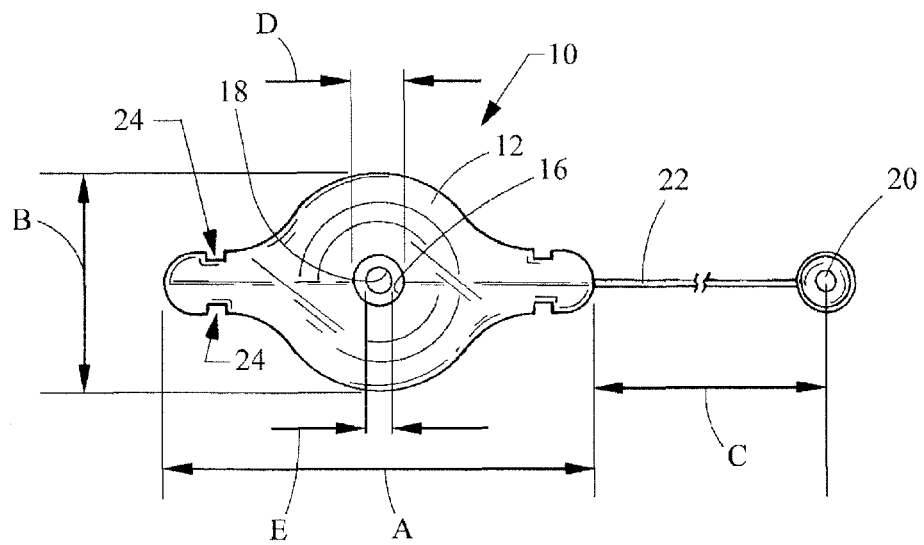
FIG. 2 is a top plan view of the in-dwelling port of FIG. 1.
Figure 3:
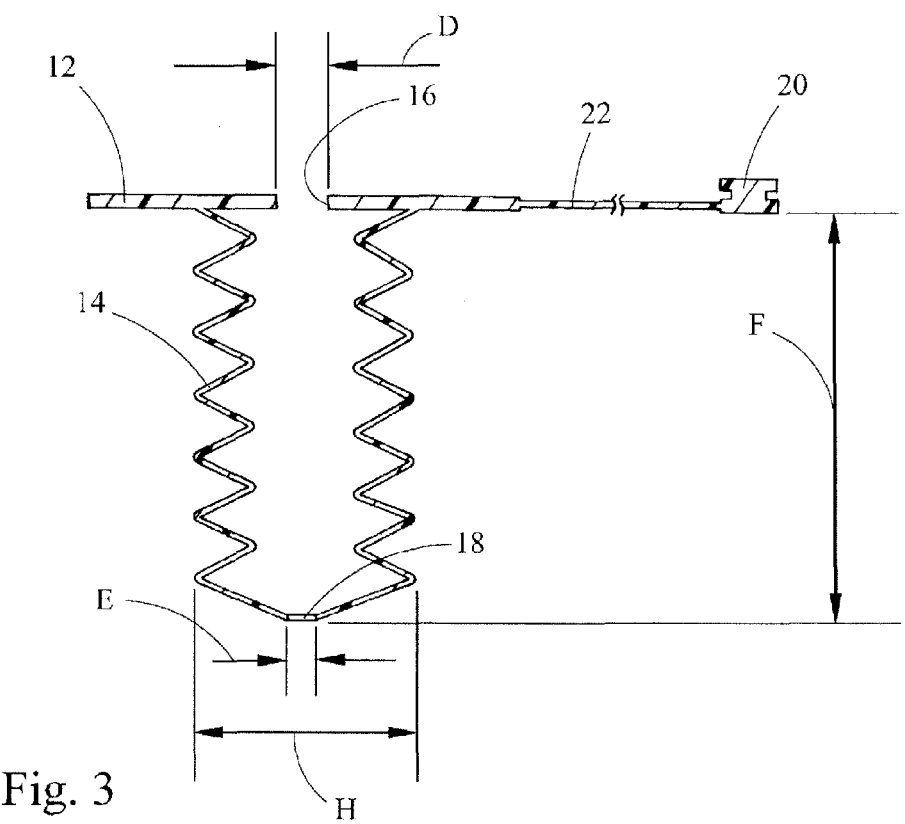
FIG. 3 is a cross-sectional side view of the port of FIG. 1.

FIGS. 1-4 illustrate one version of an in-dwelling port 10 where separation of body spaces may be required on a recurring basis. This in-dwelling port 10 may be used to reinflate the space between the abdominal wall and the organs below (peritoneal cavity). The port 10 includes an outer flange 12 and a collapsible insertion portion 14. The outer flange 12 may have a greater diameter than that of the collapsible insertion portion 14 to stabilize the port in the patient and prevent over-insertion into an incision. A proximal port opening 16 is defined by the flange 12 to allow one or more lumens or medical devices access into the collapsible insertion portion 14. A distal port opening 18 is positioned at the end of the collapsible insertion portion 14 and permits access to the body cavity.

A replaceable plug 20 is removably insertable into the proximal port opening to prevent an infection or other foreign substances to enter the body when the in-dwelling port 10 is not in use. The plug 20 may be attached to the outer flange 12 by a tether 22. The tether may be formed from the same piece of material as the outer flange, or it may be a separate material attached to the outer flange 14. The plug may be a compression-style plug that is elastic enough to fill the proximal port opening 16 when pressed in place. Alternatively, the plug 20 may be a discrete component unattached by a tether. Any of a number of other fastening means, such as threaded ends, collapsible detents or other mechanisms may also be used to connect the plug and the proximal port opening.

The outer flange may include recessed regions 24 on one or more sides. The recessed regions may be sized to provide an anchor for sutures, adhesives or other devices for holding the in-dwelling port in place on the body. The outer flange may also be held in place by having an optional adhesive surface to keep it against the skin. The adhesive surface may be islands of adhesive positioned about the underside of the flange. Alternatively, to provide a more complete seal and to help prevent deterioration of the tissue through which the in-dwelling port is inserted, a continuous ring of adhesive or adhesive material may be positioned on the underside of the flange to prevent tearing and strengthen the integrity of the tissue surface. Thus, the in-dwelling port 10 may be affixed in a number of ways, individually or collectively, by suturing the recessed regions of the flange, adhering the underside of the flange to the outer tissue surface, and even covering the flange with an adhesive bandage (regular and medicated) to help keep it in place and to further help resist infection.

Figure 4:
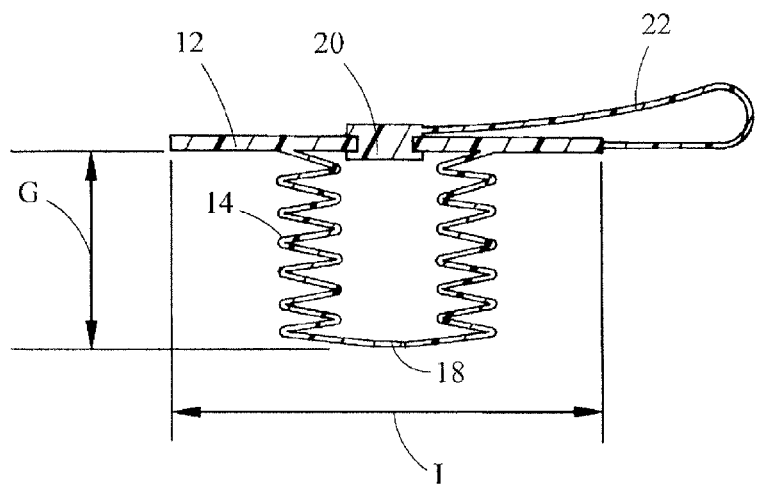
FIG. 4 is a cross-sectional side view of the port of FIG. 1 in a collapsed position.

The collapsible insertion portion 14 of the in-dwelling port 10 may be fabricated in any manner that permits it to collapse when not in use, for example in the form of a bellows or accordion-like structure. Once past the abdominal wall or other body structure, it can gently collapse back to an almost flat shape. The flat shape may assist in reducing irritation and trauma, as well as provide very little restriction to normal body motion and limited visibility of its presence. A feature of the bellows structure of the collapsible insertion portion is that it will present a reduced diameter when elongated and may more easily go through a relatively small incision or wound site, or even a natural body passage way. Once in place, the structure will allow the collapsible insertion portion to collapse into a larger diameter so as not to work itself out of the incision, wound, or body passage. Referring to FIG. 4, the collapsed state of the in-dwelling port expands the bellows portion to hold, for example, the abdomen wall between the flange 12 and the collapsible insertion portion 14 for a secure and low-profile point of re-entry.

Figure 5:
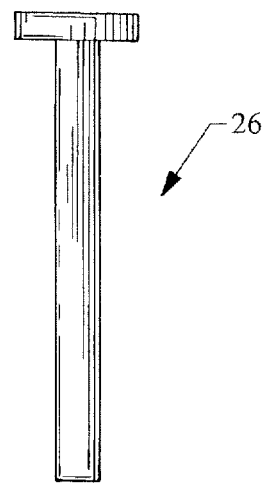
FIG. 5. is a side view of a stylus suitable for use in inserting the port of FIG. 1 into an incision.

Referring to FIG. 5, a stylus 26 is designed to fit in the collapsible insertion portion 14 via the proximal port opening 16 and extend the in-dwelling port 10 to its smallest diameter for insertion into an incision. If, for example, the in-dwelling port was intended for insertion into an abdomen wall, the stylus would first be inserted into the proximal port, extending the collapsible insertion portion and thus reducing its diameter. The distal port opening 18 may be provided with a smaller diameter than the proximal port opening 16 so that the stylus 26 remains in the collapsible insertion portion during insertion. A physician may then push the in-dwelling port into position from outside the abdomen wall and into the peritoneum, for example via a trocar wound (not shown).

Once inserted, and optionally secured at the flange to the abdomen, the stylus 26 would typically be removed and one or more lumens may be introduced and later reintroduced, through the in-dwelling port. The in-dwelling port 10 may allow for the insertion of medical devices after placement by maintaining one or more access lumens to pass a medical device through it such as a catheter, or a small needle or trocar, an optical endoscope, an operative instrument or any number of surgical, diagnostic, or palliative devices.

When all lumens in the port 10 are removed and the port is not in use, the collapsible insertion portion will collapse down and allow the abdomen wall to collapse to a more relaxed position that may be substantially close to its pre-insertion shape. The plug 20 may then be inserted to provide a barrier to contaminants. Having a way to allow the separation (or re-separation) of the abdominal wall or cavity from the organs below for purposes of examination, application of medicines, or even operative tasks is desirable and is usually accomplished by insufflation of the peritoneal space. Because the port is intended for access to the bodily space for the purpose of re-expanding the separation of one layer or body structure from another the port also permits the body structure to return to its substantially normal (collapsed) position.

Figure 6:
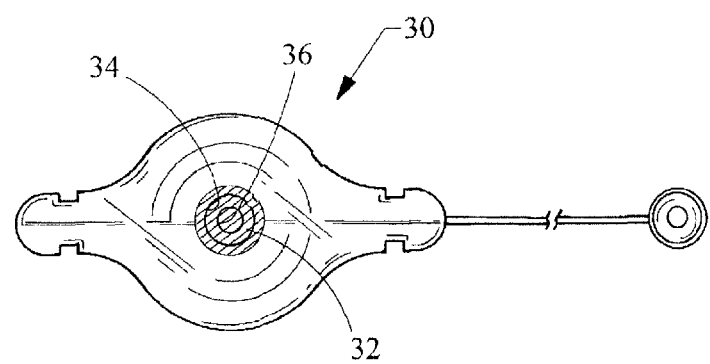
FIG. 6 is a top plan view of an alternative embodiment of the in-dwelling port of FIG. 1.
Figure 7:
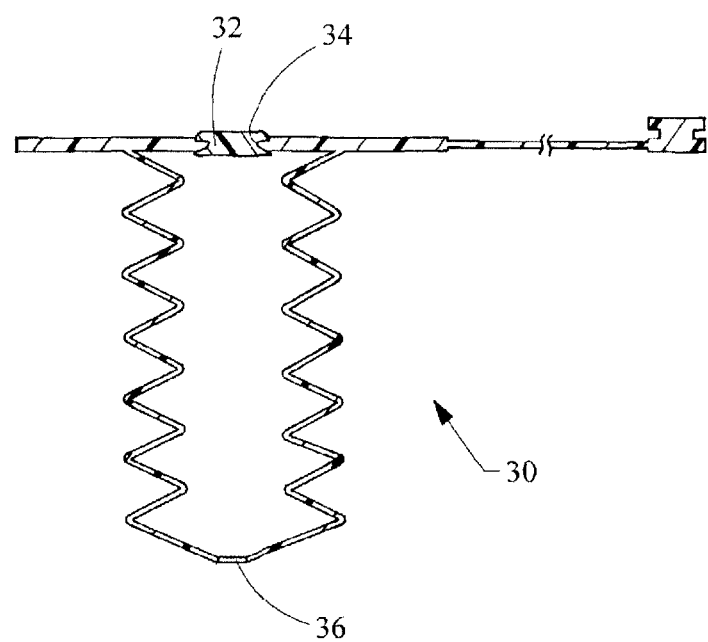
FIG. 7 is a cross-sectional side view of the port of FIG. 6 in an elongated position.

An alternative embodiment of the in-dwelling port 30 is shown in FIGS. 6-7. In this arrangement, a re-sealable membrane 32 is positioned across the proximal port opening 34. A needle or other sharp-ended introducing device may be used to pierce the membrane 32 or surface and introduce a lumen or instrument through the membrane and subsequently into the body via the distal port opening 36. The membrane would reseal itself after removal. This pierceable membrane or cover may be manufactured from any of a number of materials, for example polysoprene, isoprene or silicone. In an alternative embodiment, the in-dwelling port may have a second proximal port opening that could be connected to a filter in order to release pressure from an expanded space, for example the peritoneum during a laparoscopic procedure, without permitting organisms to be released into the air.

Figure 8:
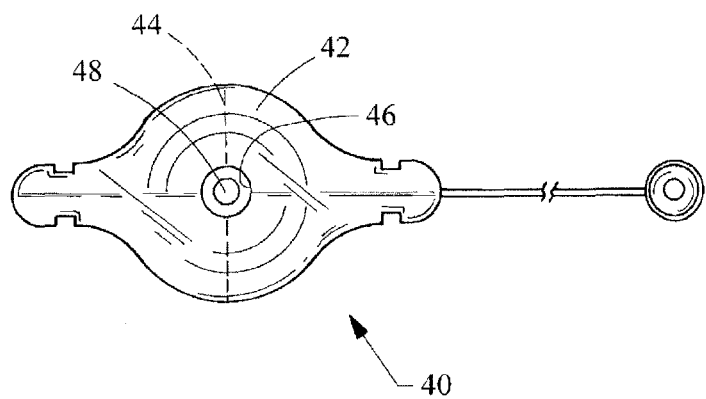
FIG. 8 is a top plan view of a second alternative embodiment of the in-dwelling port of FIG. 1.
Figure 9:
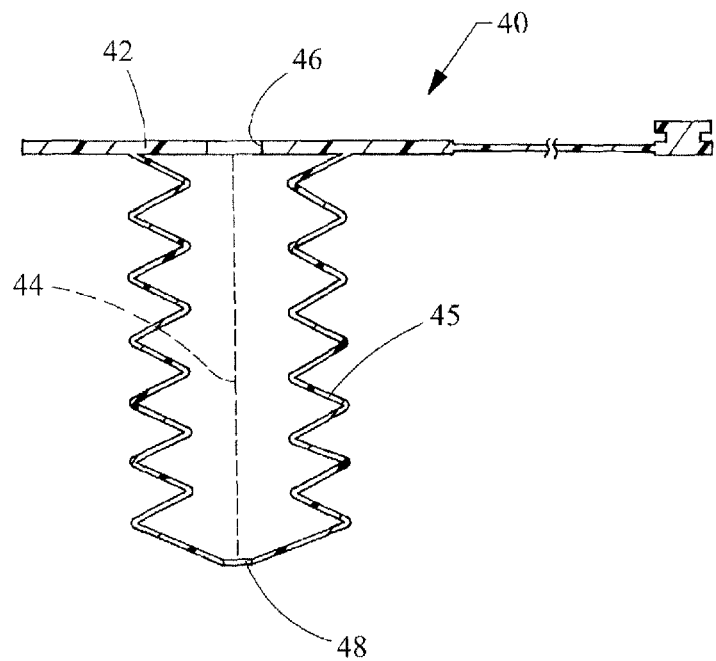
FIG. 9 is a cross-sectional side view of the port of FIG. 8 in an elongated position.

In an alternative embodiment shown in FIGS. 8-9, the in-dwelling port 40 may have a tear-away seam 44 disposed along the entire length of the port. The seam 44 may traverse the flange 42 and the collapsible insertion portion 45 to form a continuous line of perforations from the proximal port opening 46 to the distal port opening 48. In one embodiment, the seam 44 may be a line of perforations extending longitudinally down the device from proximal 46 to distal 28 port opening, multiple parallel lines of perforations to allow for tearing the in-dwelling port from one or more sides of the flange 42, or any desired pattern of perforations to allow segmented destruction and removal of the in-dwelling port. In alternative embodiments, the lines of perforations may be other types of weakened seams defining a continuous line of weakened or reduced thickness material that permit for a substantially clean tear when a user desires to remove the in-dwelling port.

One advantage of an in-dwelling port as shown in FIGS. 8-9 with a tear-away seam is that a new in-dwelling port may be inserted into an old in-dwelling port already positioned in a body and the old port could be removed by splitting and pulling out the old port. Alternatively, the old port could pulled into a sleeve device and removed, the sleeve serving to keep the space open to place a new port in place of the old port, or even a tool or a finger could be pushed alongside the old port while a new port is positioned next to the tool or finger, and inserted.

The in-dwelling ports in FIGS. 1-9 are shown with one lumen through the center. In other implementations, two or more lumens may be fabricated so that more than instrument could be inserted into it, or one lumen could be attached to a pressure source such as an insufflator and the other to a suction source, or a commercially available pressure relief device (such as manufactured by Smart products), or a mini-endoscope may be inserted into one lumen an and instrument or catheter or some other operative device may be inserted into another. The device is not limited to a single useful lumen, and multiple lumens could be utilized with many other medical devices seeking entry into the body space. Other uses for the lumen(s) may include applications requiring the insertion of a fluid catheter, the use of an aerosolization or nebulizing device for the purpose of coating or treating organ cavity.

As shown in FIGS. 10-12, an in-dwelling port 50 may be constructed with two proximal openings 52 that each lead to a respective half of the interior of a single collapsible insertion portion 62. Each proximal opening 52 may have its own removable plug 54 attached to the flange 64 by respective tethers 56. A collapsible partition 60 extending through the interior of the area enclosed by the collapsible insertion portion 62 defines two separate access paths 66 terminating at respective distal openings 58. Although the access paths 66 are shown as equal in size in FIGS. 10-12, access paths of unequal size or more than two paths in the single collapsible portion 62 are contemplated as well.

Figure 13:
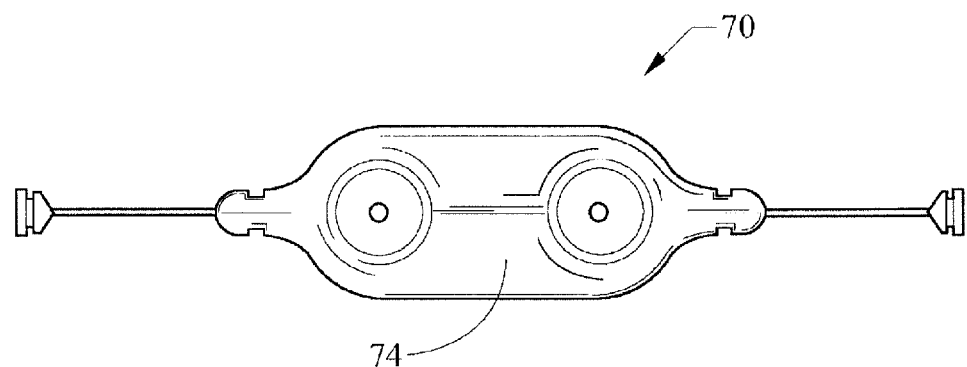
FIG. 13 is a top plan view of a fourth alternative embodiment of the in-dwelling port of FIG. 1.
Figure 14:
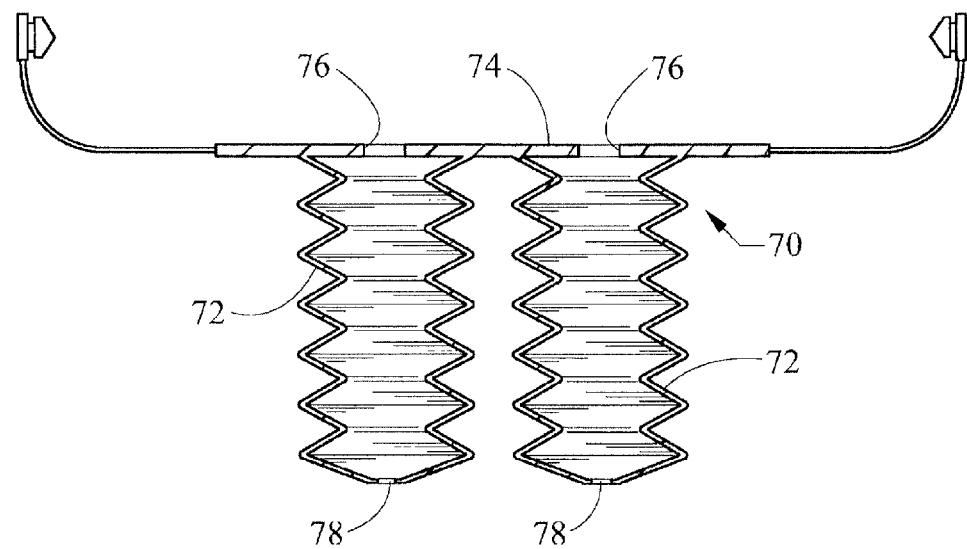
FIG. 14 is a cross-sectional side view of the port of FIG. 13 in an elongated position.

FIGS. 13 and 14 illustrate another version of an in-dwelling port 70 for allowing access for multiple devices such as noted above. In the version of FIGS. 13-14, two completely separate collapsible insertion portions 72 are formed in a single flange member 74. Each collapsible portion has its own proximal and distal opening 76, 78, where the proximal openings 76 may have a greater radius than the distal openings 78 or may be covered with a membrane suitable for piercing by a needle or other sharp instrument. Additionally, one or both collapsible portions may be partitioned internally as shown in FIGS. 10-12 to provide separate access for even more devices or instruments into a body cavity.

Figure 15:
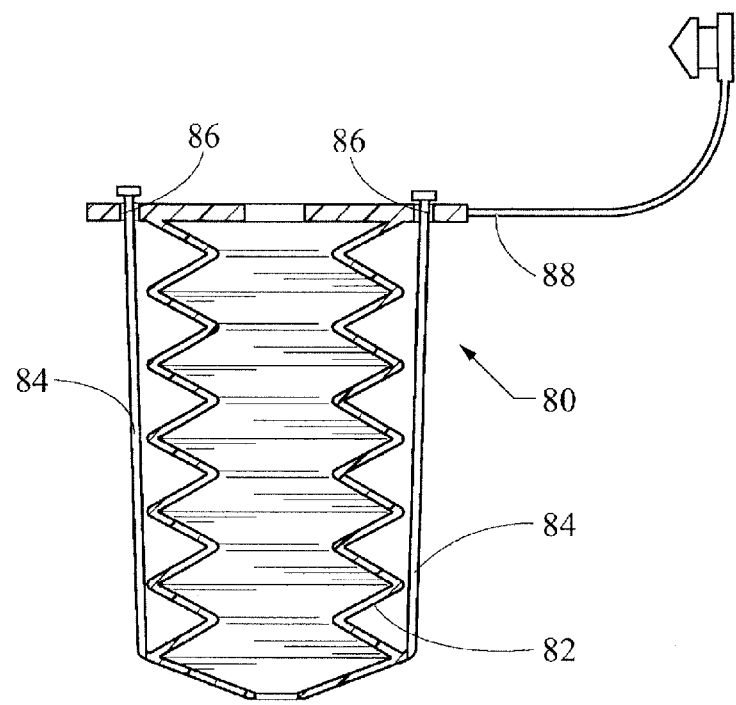
FIG. 15 is a cross-sectional side view of a fifth alternative embodiment of the port of FIG. 1 in an elongated position.
Figure 16:
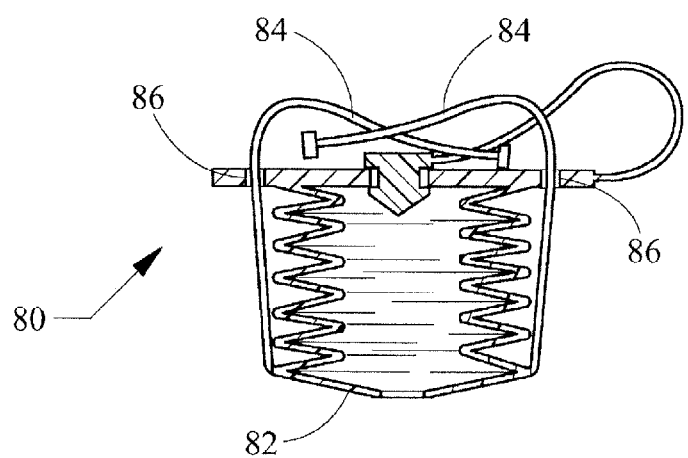
FIG. 16 is a cross-sectional side view of the port of FIG. 15 in a collapsed position.

Although the example of in-dwelling ports described above include collapsible insertion portions, shown as bellows, that are expandable into a body cavity, there may be a need to insure that the collapsible insertion portion or bellows of the device stays up to the distal surface (i.e. the interior surface) of the tissue or organ into which the device is inserted. FIGS. 15-16 illustrate an implementation of an in-dwelling port 80 that allows for the collapsible insertion portion 82 to remain secure, and prevent it from "relaxing" or loosening and becoming partially extended in the bodily cavity. This is accomplished by having one or more threads or tethers 84 attached to the distal portion of the insertion portion, which can be used to draw-up or retract the collapsible insertion portion 82, either through holes 86 in the top flange 88, or along the outside of the collapsible insertion portion 82 and the outside(s) of the top flange to be secured by some means such as tying, suturing, taping or any other method of securing the tether(s) 84 in such a way as to keep the collapsible insertion portion 82 collapsed, or loosening them to allow the collapsible insertion portion 82 to be expanded. The tethers 84 can be constructed of the same material as the in-dwelling port 80, from thread, or from any other flexible thin material. It could be accomplished with one or more such tethers 84. The tethers 84 can be attached to the collapsible insertion portion 82 in the molding process, by heat sealing (melting), tying, gluing, or any other method of attaching the tethers to the collapsible insertion portion of the device.

In yet additional alternative embodiments, where additional rigidity of the collapsible insertion portion may be desired, a stylus such as shown in FIG. 5 may include a central bore through which instruments or lumens may be inserted. Such a modified stylus may remain in the in-dwelling port during a procedure and removed to allow the in-dwelling port to collapse when not in use Any of the in-dwelling port versions described above may be coated or impregnated with antibacterial and or antimicrobial medications to prevent infection from occurring during its time in place. Such a coating for example could consist of, but is not limited to, Rifamacin, Rifampin, Minocycline, silver sulfadiazine, or Bardex R IC.

The in-dwelling port may be constructed of a resilient material that has the ability to reform its shape or accept a "retracted" shape after it is in place. Suitable materials include, but are not limited to, silicone, rubber, latex, nylon, and fabric like materials. Although any number of in-dwelling port sizes and dimensions are contemplated, and may vary depending on intended use, the example shown in FIG. 2 may have a flange major axis length A of 1.75 inches, a flange minor axis length B of 0.875 inches, and a tether length C of 0.875 inches. The proximal port opening diameter may be 0.196 inches and the distal port opening may be 0.112 inches. Accordingly, the stylus used to insert this specific version of the in-dwelling port would need to have a minimum diameter of greater than 0.112 inches and a maximum diameter of less than 0.196 inches. Referring again to FIGS. 3 and 4, the collapsible insertion portion in this example may have a collapsed depth G of 0.375 inches and a maximum extended depth F of 5.0 inches for a greater than 5 to 1 ratio. The extended diameter H of the collapsible insertion portion is preferably less than the collapsed diameter I, however the ratio may vary depending on, for example, the number and length of the folds that form the bellows or accordion-like structure of the collapsible insertion portion.

Referring now to FIGS. 17-20, an alternative embodiment of an in-dwelling port is disclosed. The in-dwelling port 100, as seen in FIG. 17A, includes a flange 102 and an insertion portion 104, but differs from the prior embodiments in that the insertion portion 104 incorporates both a collapsible portion 106 and a non-collapsing portion 108. The non-collapsing portion 108 connects directly to the flange 102 and may provide for a tighter fit against an opening of the abdominal wall. The non-collapsible portion 108 can provide a firmer fit and better maintain an opening for subsequent re-introduction of medical equipment into the in-dwelling port 100. The embodiment of FIGS. 17-18 also includes a pair of tethers 110 that connect to the distal end of the insertion portion 104, specifically the distal end of the collapsible potion 106 of the insertion portion 104, to aid in retraction of the collapsible portion 106 of the insertion portion 104 when the in-dwelling port is not in use. The collapsible region 106 is collapsible down to the end of the non-collapsible portion by virtue of the bellows structure of the collapsible portion. Although a bellows structure is illustrated for the collapsible portion 106, or collapsible structures, including but not limited to collapsible overlapping ring sections or stretchable materials, are contemplated in different embodiments.

Figure 17A:
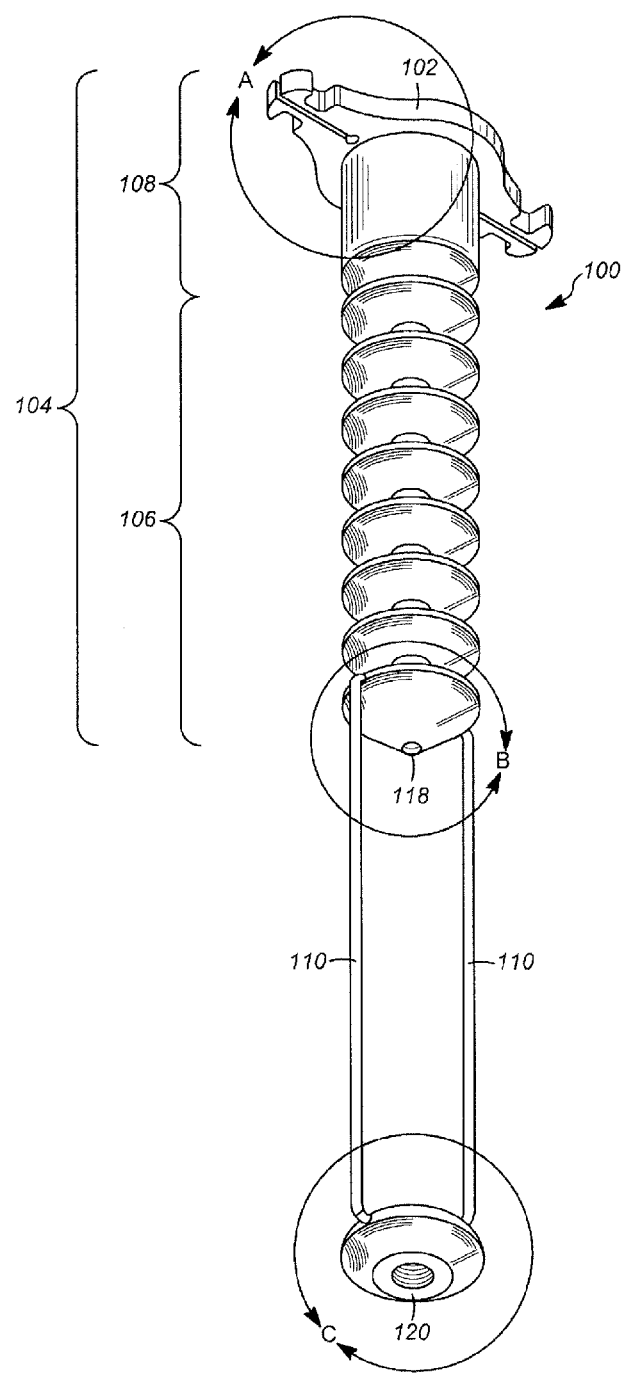
FIG. 17A is a bottom perspective view of an alternative embodiment of the in-dwelling port of FIG. 1.
Figure 17B:
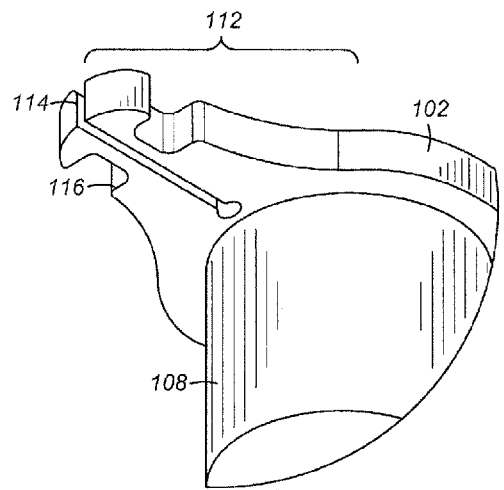
FIG. 17B is a sectional view of the in-dwelling port of FIG. 17A taken along line A in FIG. 17A.
Figure 17C:
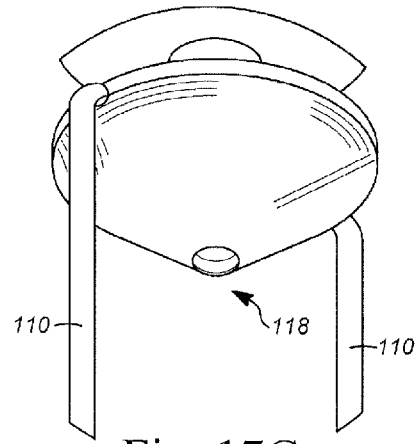
FIG. 17C is a sectional view of the in-dwelling port of FIG. 17A taken along line C in FIG. 17A.
Figure 17D:
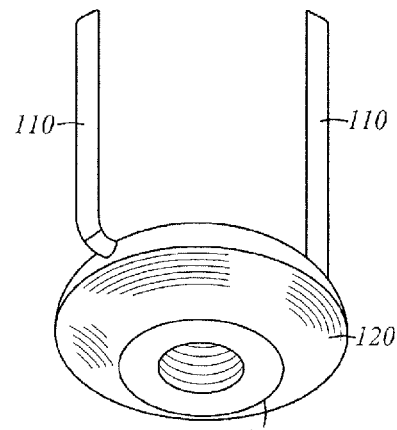
FIG. 17D is a sectional view of the in-dwelling port of FIG. 17A taken along line B in FIG. 17A.
Figure 18A:
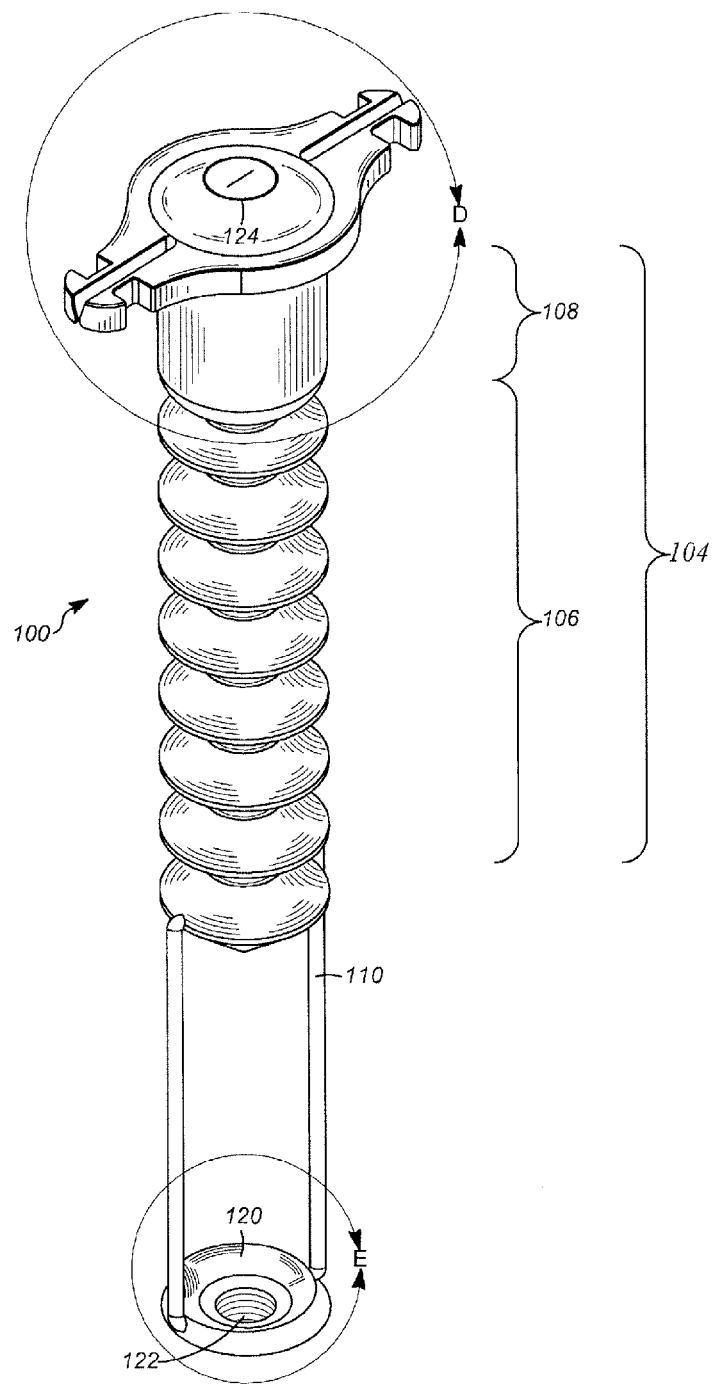
FIG. 18A is a top perspective view of the in-dwelling port of FIG. 17A.
Figure 18B:
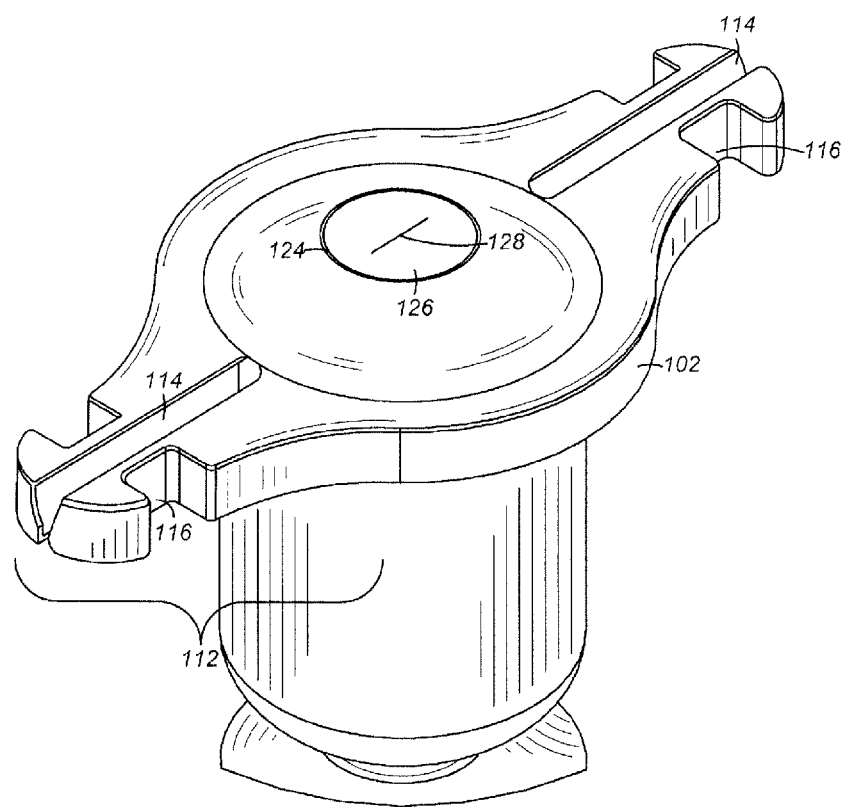
FIG. 18B is a sectional view of the in-dwelling port of FIG. 18A taken along line D in FIG. 18A.
Figure 18C:
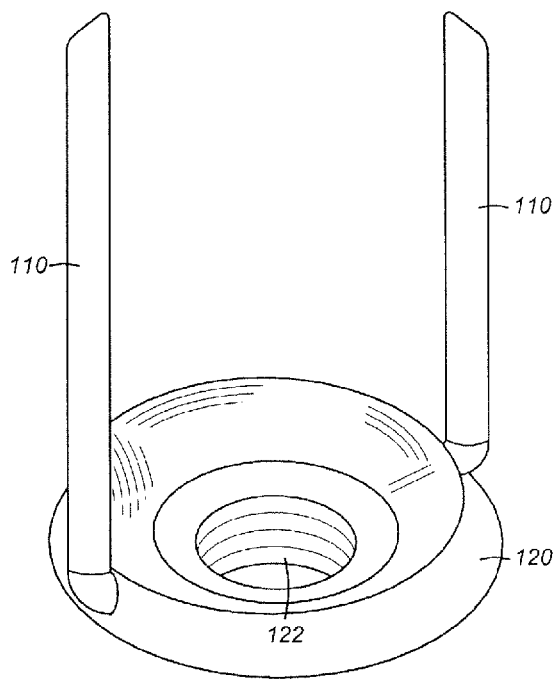
FIG. 18C is a sectional view of the in-dwelling port of FIG. 18A taken along line E in FIG. 18A

As shown in FIG. 17B, each arm 112 of the flange 102 includes a tethered guide slot 114 extending from the end of the arm 112 toward the center area of the flange 102 outside of the non-collapsible portion 108. A pair of recessed regions 116 are positioned toward the ends of the arms 112 outside of the tethered guide slots 114 to allow for sutures or other fastening mechanisms to help hold the flange 102 against the skin of a patient while the in-dwelling port 100 is installed in a patient. When the in-dwelling port 100 is assembled for use, the tethers 110 are each positioned in a respective tether guide slot 114. The distal end of the collapsible region 106 of the insertion portion 104 includes a distal port opening 118 (see FIG. 17C). A difference between the in-dwelling port of FIGS. 17-18 and that of the earlier tether version shown in FIGS. 15 and 16 is the addition of a retention ring 120 that is attached to the tethers 110 and includes a central textured passage 122 as best seen in FIG. 17D. As shown in FIGS. 18A-18C, the proximal port opening 124 of the in-dwelling port 100 is covered by a membrane 126 having a predefined slit 128 configured to resealably close after removal of medical equipment from the proximal port opening 124. In one embodiment, the proximal port opening has a larger diameter than the distal port opening 118. In yet other embodiments, the membrane 126 may be a pierceable membrane rather than a pre-slit membrane. Multiple slits arrayed in a radial pattern may be used, and other self-closing or hinged configurations are also contemplated over the proximal port opening 124. An embodiment with no membrane, and instead using a tethered plug sized to resealably close the proximal port opening, is also contemplated.

Figure 19:
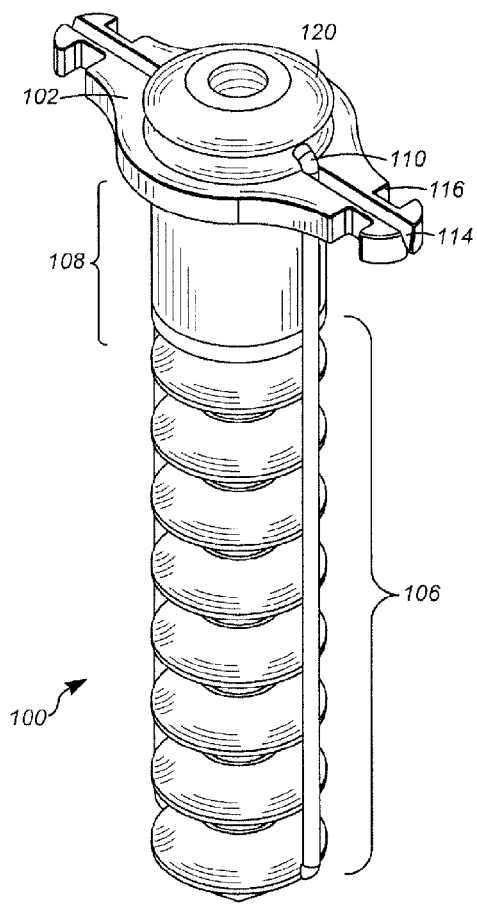
FIG. 19 is a perspective view of the in-dwelling port of FIG. 18A in an assembled and extended position.
Figure 20:
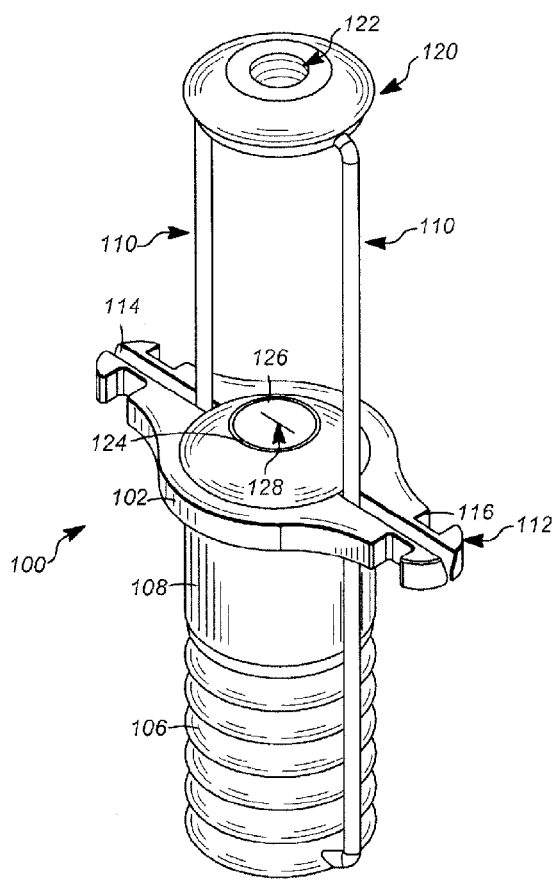
FIG. 20 is a perspective view of the in-dwelling port of FIG. 18A in an assembled and retracted position.

For ease of reference, FIGS. 17-18 illustrate an expanded view of in-dwelling port 100 prior to configuration for insertion into a body cavity, while FIGS. 19-20 show the orientation of the in-dwelling port assembled and ready for use. Referring now to FIGS. 19-20, when the in-dwelling port 100 is assembled and ready for use, the retaining ring 120 is positioned on the opposite side of the flange 102 from the insertion portion 104 with the tethers 110 positioned respectively in the tether guide slots 114 on opposite sides of the proximal port opening 124. FIG. 19 illustrates the fully extended position for the in-dwelling port 100 where the maximum throw of the tether 110 is limited by the retention ring 120, where the retention ring 120 contacts the outside portion of the flange 102. FIG. 20 illustrates the in-dwelling port 100 when it is in a collapsed position and the collapsible region 106 has been retracted by pulling on the tethers 110 via the retention ring 120 attached to the end of the tethers 110 and located outside of the flange 102. An advantage of the retention ring 120 being attached to both tethers 110 is that the collapsible portion 106 of the insertion portion 104 may be retracted evenly and symmetrically. In one embodiment, the tethers are sized to slide freely in the tether guide slots. In other embodiments, the diameter of the tethers and the width of the slot are sized to provide sufficient friction to maintain a current position of the collapsible portion absent a force applied to the retention ring 120 to retract, or a force applied by an introducer or medical instrument inserted into the in-dwelling port to expand, the collapsible portion. The tethers may be made from a rigid material or a flexible material in different embodiments. In one embodiment, the hardness of the tether material may be in the range of 30-85 durometer on the Shore A scale, and more preferably in the range of 60-65 durometer on the Shore A scale.

Although not required, the in-dwelling port 100 of FIGS. 17-20 may be used with an introducer 200 as illustrated in FIGS. 21-22. Similar to the stylus 26 of FIG. 5, the introducer 200 is designed to fit into the proximal port opening 124 and be extended into the in-dwelling port 100 so that the distal end of the collapsible portion 106 of the insertion portion 104 is extended by contact of the introducer 200 to the inside of the collapsible portion 106 surrounding the distal port opening 118. Again, the proximal port opening 124 is sized larger than the distal port opening of the in-dwelling port such that the introducer may fit within the proximal opening through the slit and the distal end 214 of the introducer, which is at the far end of the extended tube portion 204 is larger than the distal port opening of the in-dwelling port and will not pass through the distal port opening Referring to FIG. 21A, the introducer 200 may have any of a number of additional features associated with it. The introducer 200 may include an upper housing 202 aligned with an extended tube portion 204 such that one or more lumens may be passed through one or more openings defined by the upper housing and the extended tube. The upper housing 202 may include a first proximal opening 206 for receiving medical instrumentation and a second proximal opening 208 for receiving additional instrumentation or for connecting to a fluid source, such as an insufflation gas or irrigation liquid supply.

As shown in FIG. 21B, the extended tube portion 204 of the introducer 200 may include dimensioned ribs 210 that are evenly spaced and have a diameter greater than the outer diameter of the extended tube 204. Optional markings 212 may also be included next to one or more of the dimensioned ribs to indicate a depth of insertion from the distal end 214 of the introducer 200. The distal end of the introducer 202 is sized with a greater diameter than the diameter of the distal opening 118 of the in-dwelling port 100 such that the in-dwelling port may extended by contact of the distal end of the introducer 202 against the inside of the in-dwelling port 100. Additionally, the dimensioned ribs 210 that extend beyond the diameter of the main shaft of the extended tube portion 204 are sized to fit within the proximal port opening 124 of the in-dwelling port 100.

Figures 23, 24:
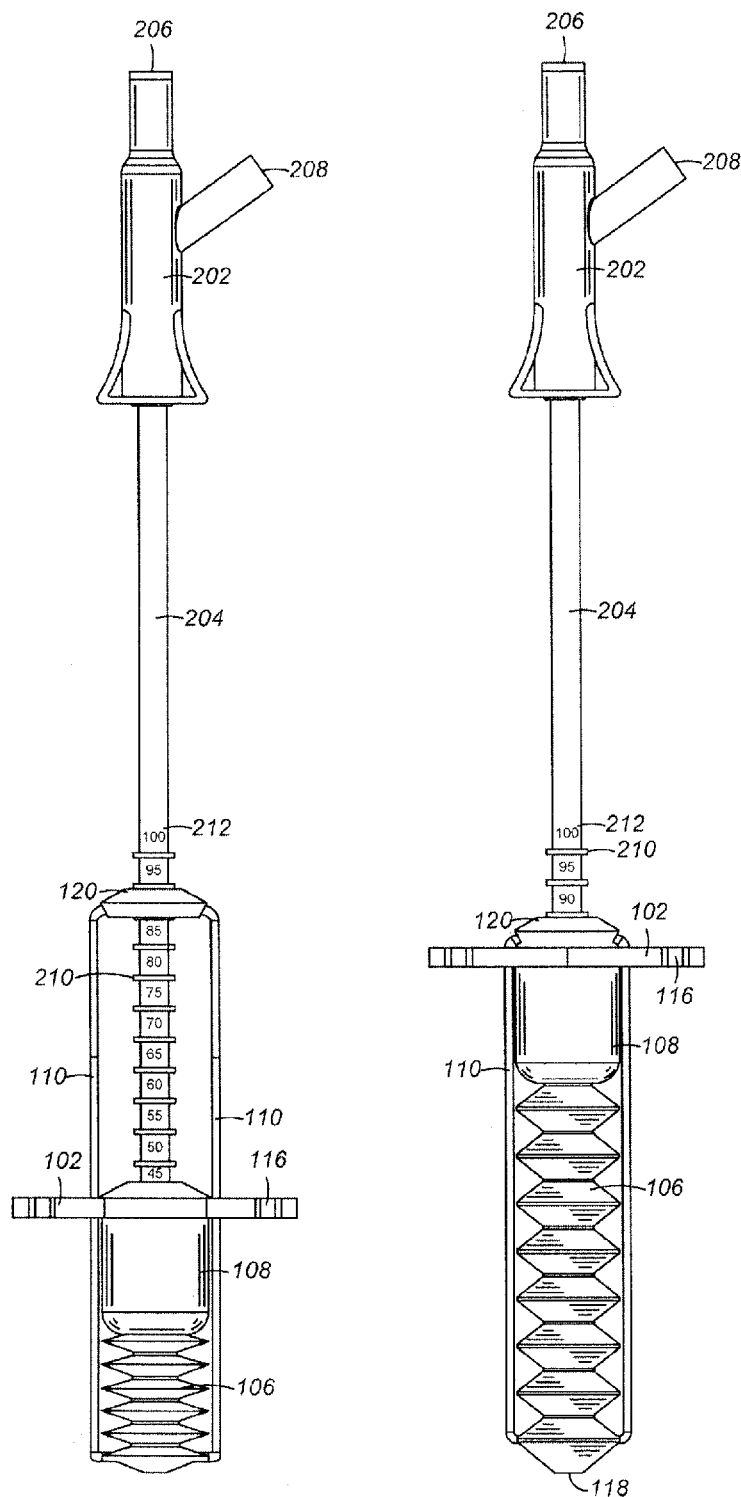
FIG. 23 illustrates a system of the inserter of FIG. 21A positioned in the in-dwelling port of FIG. 19 when the in-dwelling port is in a retracted position.
FIG. 24 illustrates a system of the inserter of FIG. 21A positioned in the in-dwelling port of FIG. 19 when the in-dwelling port is in an extended position.

Operation of the in-dwelling port of FIGS. 17-20, in cooperation with an introducer such as the introducer 200 of FIGS. 21-22, is now described with respect to FIGS. 23-24. The in-dwelling port 100, when assembled for use, may be packaged such that the tethers 110 are positioned in the tether guide slots 114 on the flange 102. The bellows of the collapsible region 106 of the insertion portion 104 may be in, or placed in, a collapsed position and the distal end of the introducer 200 would then be inserted into the donut-shaped retention ring 120 through the textured passage 122 of the retention ring 120. In one embodiment, the spacing of the dimensioned ribs 210 on the introducer 200 may be such that the thickness of the retention ring 120 is captured between adjacent dimensioned ribs. Alternatively, the textured passage 122 of the retention ring 120 may be sized with recessed circumferential rings, or extended detents or rings, such that an individual dimensioned rib 212 would be captured within the textured passage 122. In yet other alternative implementations, an introducer without any dimensioned ribs may be used and the fictional fit of the retention ring 120 with or without a texture in the passageway 122 may frictionally fit against the outside of the introducer.

Once the retention ring 120 is attached to the desired portion (e.g., a desired portion being the portion that will allow for intended insertion depth of the introducer) a catheter, instrument, scope or whatever other medical device that is desired to be introduced through the introducer 200 may be pushed down into the port 100, where the bellows of the collapsible region 106 would be expanded to the desired length within an abdominal cavity. The extension of the collapsible portion may be limited by the retaining ring contacting the flange (FIG. 24). Once the procedure for which the in-dwelling port 100 was needed is completed, the introducer 200 may be removed and the retaining ring 120, held in place against the introducer by any of the mechanisms noted above, or by a user maintaining a finger between the retaining ring and the flange, may pull with it the tethers and raise the collapsible portion towards the flange until the collapsible portion is sufficiently collapsed against the non-collapsible portion 108 (FIG. 23). After the collapsible portion has been fully retracted and the introducer is fully removed from the port, the port may be secured to the top surface of the abdomen (e.g., the outer surface of the skin of a patient) either by an adhesive surface on the bottom side of the flange 102, by placing stitches into the recessed portions 114 of the flange 102 or by folding and taping the tether 110 and retaining ring 120 and the complete flange surfaces to the patient in order to help prevent misplacement or other movement of the port. Securing of the port 100 to prevent movement will also likely reduce chance of infection.

As in the embodiments previously discussed, the material for the in-dwelling port may be silicone or other flexible or somewhat-flexible material. In alternative embodiments, the in-dwelling port may be constructed from a polycarbonate or metal material, or a combination of silicone, polycarbonate and/or metal material. The in-dwelling port 100 may be radio opaque and may have printed indicators showing size or position. Furthermore, the in-dwelling port may be made of, or coated with an antimicrobial substance, or all of the above options combined.

The embodiment of FIGS. 17-24 may provide a more efficient and reliable mechanism for allowing the collapsible portion to collapse in a straighter and more repeatable manner. The non-collapsible portion of the insertion portion may provide added security to the positioning of the in-dwelling port in an incision and may provide a better opening for re-introduction of the introducer 200 than a fully collapsible insertion portion. The tether guides in the flange may assist in the prevention of twisting of the collapsible portion and provide improved repeatability of movement and positioning of the collapsible portion. Finally, the pre-slit membrane may assist in preventing contamination and infection, while providing a repeatedly usable opening that only need be covered by a common adhesive bandage between insertions of an introducer and or medical instrument.

The dimensions (such as extended and collapsed length, and the diameter (exterior or interior) of the collapsible portion) of the in-dwelling may be varied according to the desired use. In one embodiment, the proximal port opening 124 and distal port opening 118 may have the same respective diameters as described with respect to the embodiment of FIGS. 1-3. The extendibility of the collapsible portion may such that the fully extended length is a factor of 2-3 times the fully collapsed length. Similarly, the length of the inserter 200 may be sized to permit full extension of the in-dwelling port 100, if desired, with graduated markings 212 and/or ribs along the hollow tube of the extended tube portion 204 sufficient to guide a user to the exact depth of the distal port opening relative to the flange at the outer surface of the body cavity it is installed on.

The different length or diameter in-dwelling port designs may be selected based on patient body type or incision location. For example, it is contemplated that a set of different size in-dwelling ports may be produced to allow caregiver selection at the time of use based on patient characteristics and desired incision location. The range of lengths achievable from a particular in-dwelling port having both non-collapsible and collapsible portions may be, in one embodiment, 30 mm-82 mm inclusive of the collapsible and non-collapsible portion lengths, and the outer diameter of the insertion portion may be in the range of 5 mm-11 mm. As noted previously, other in-dwelling port range lengths are contemplated. Although any of a number of outer diameter ratios between the outer diameter of the non-collapsing portion and the collapsible portion are contemplated, in one embodiment, the maximum outer diameter of the collapsible portion 106, when in the collapsed position (i.e., where the collapsible portion is at its shortest, retracted length), is preferable greater than the outer diameter of the non-collapsing portion. In one implementation, the diameter of the collapsible portion in a collapsed position may be 20%-50% greater than the diameter of the non-collapsing portion. This disparity in diameters may aid in keeping the in-dwelling port from sliding out of the incision when not in use because the collapsible portion, when collapsed, may have a greater diameter that the incision through which the insertion portion was inserted.

It is therefore intended that the foregoing detailed description be regarded as illustrative rather than limiting, and that it be understood that it is the following claims, including all equivalents, that are intended to define the spirit and scope of this invention.

I claim:

1. An in-dwelling port for permitting access into a body, the port comprising:
an external portion configured for placement outside of an incision and defining a proximal port opening; and
an insertion portion having a non-collapsible portion attached to the external portion and positioned in a substantially coaxial relationship to the proximal port opening, and a collapsible portion attached to the non-collapsible portion, the collapsible portion defining a distal port opening and repeatably adjustable between an elongated position and a collapsed position, wherein the collapsible insertion portion comprises a collapsed length that is shorter than an extended length; and wherein the distal port opening has a diameter less than any diameter of the non-collapsible portion.

2. The port of claim 1, further comprising a membrane having a reclosable slit sized to seal the proximal port opening.

3. The port of claim 1, wherein the insertion portion comprises an antimicrobial material.

4. The port of claim 1, wherein the insertion portion comprises a coating of antimicrobial material.

5. The port of claim 1, further comprising a tear-away seam extending at least a portion of a length of the collapsible insertion portion and at least a portion of a width of the external portion.

6. The port of claim 1, further comprising an adhesive positioned along an underside of the external portion and configured to adhere to tissue surrounding an incision through which the collapsible insertion portion may be inserted.

7. An in-dwelling port for permitting access into a body, the port comprising:
an external portion configured for placement outside of an incision and defining a proximal port opening;
an insertion portion having a non-collapsible portion attached to the external portion and positioned in a substantially coaxial relationship to the proximal port opening, and a collapsible portion attached to the non-collapsible portion, the collapsible portion defining a distal port opening and repeatably adjustable between an elongated position and a collapsed position, wherein the collapsible insertion portion comprises a collapsed length that is shorter than an extended length;
wherein the external portion comprises a flange having an arm extending radially away from the proximal port opening, the arm defining a recessed region for receiving a suture; and
wherein the flange further comprises a slot longitudinally extending a length of the arm, the slot having an open end at a distal end of the slot and a closed end at a proximal end of the slot adjacent the proximal port opening.

8. The port of claim 7, further comprising a membrane having a reclosable slit sized to seal the proximal port opening.

9. The port of claim 7, wherein the insertion portion comprises an antimicrobial material.

10. The port of claim 7, wherein the insertion portion comprises a coating of antimicrobial material.

11. An in-dwelling port for permitting access into a body, the port comprising:
an external portion configured for placement outside of an incision and defining a proximal port opening;
an insertion portion having a non-collapsible portion attached to the external portion and positioned in a substantially coaxial relationship to the proximal port opening, and a collapsible portion attached to the non-collapsible portion, the collapsible portion defining a distal port opening and repeatably adjustable between an elongated position and a collapsed position, wherein the collapsible insertion portion comprises a collapsed length that is shorter than an extended length;
wherein the external portion comprises a flange having an arm extending radially away from the proximal port opening, the arm defining a recessed region for receiving a suture; and
at least one tether having a distal end and a proximal end, wherein the distal end of the tether is connected to a distal section of the collapsible insertion portion and the proximal end is connected to a retaining member positioned on a side of the flange opposite the insertion portion.

12. The port of claim 11, further comprising a tear-away seam extending at least a portion of a length of the collapsible insertion portion and at least a portion of a width of the external portion.

13. The port of claim 11, further comprising an adhesive positioned along an underside of the external portion and configured to adhere to tissue surrounding an incision through which the collapsible insertion portion and the non-collapsible insertion portion may be inserted.

14. An in-dwelling port for permitting access into a body, the port comprising:
an external portion configured for placement outside of an incision and defining a proximal port opening; and
an insertion portion having a non-collapsible portion attached to the external portion and a collapsible portion attached to the non-collapsible portion, the collapsible portion comprising a flexible bellows having a first end connected with the non-collapsible portion and defining a distal port opening opposite the first end, wherein a diameter of the distal port opening is less than a diameter of the proximal port opening; and
at least two tethers, each of the tethers attached at a first end to the collapsible portion adjacent the distal port opening, and attached at a second end to a retaining structure positioned on an opposite side of the external portion as the insertion portion, wherein the retaining structure is movable relative to the external portion, and wherein the at least two tethers are configured to retract the collapsible portion of the insertion portion in response to a movement of the retaining structure away from the external portion.

15. The port of claim 14, wherein the external portion and the insertion portion each comprise an antimicrobial material.

16. The port of claim 14, wherein the external portion comprises at least one tether guide positioned to guide movement of the at least two tethers through the external portion.

17. The port of claim 16, wherein the at least one tether guide is a slot in the external portion outside the proximal port opening of the port.

18. The port of claim 14, further comprising a membrane having a reclosable slit sized to seal the proximal port opening.

19. The port of claim 14, wherein the insertion portion comprises an antimicrobial material.

20. An in-dwelling port system for permitting access into a body, the system comprising:
an in-dwelling port, the in-dwelling port comprising:
an external portion configured for placement outside of an incision and defining a proximal port opening;
an insertion portion configured for placement into the incision, the insertion portion having a non-collapsible portion attached to the external portion and a collapsible portion attached to the non-collapsible portion, the collapsible portion comprising a flexible bellows having a first end connected with the non-collapsible portion and defining a distal port opening opposite the first end, wherein a diameter of the distal port opening is less than a diameter of the proximal port opening; and a retraction assembly attached to the insertion portion, the retraction assembly comprising at least two tethers and a retaining structure, the at least two tethers connected to the collapsible portion at a first end and attached at a second end to the retaining structure, wherein the retaining structure is positioned on an opposite side of the external portion as the insertion portion, wherein the tethers are configured to retract the collapsible portion of the insertion portion in response to a movement of the retaining structure away from the external portion;

an inserter, the inserter comprising:

a hollow tube including a proximal end sized to receive a medical instrument and a distal end having a diameter less than a diameter of the proximal port opening and greater than a diameter of the distal port opening; and a plurality of ribs spaced positioned along the hollow tube;

and wherein the retaining structure of the retraction assembly is sized to fit on the hollow tube of the inserter such that removal of the inserter from the proximal port opening results in retraction of the collapsible portion via the at least two tethers attached to the retaining structure.

\* \* \* \* \*